United States Patent [19]

Light et al.

[11] 3,989,760

[45] Nov. 2, 1976

[54] TRICYCLIC ALCOHOLS AND LITHIUM SALTS THEREOF

[75] Inventors: Kenneth K. Light, Long Branch, N.J.; Edward J. Shuster, Brooklyn, N.Y.; Joaquin F. Vinals, Red Bank; Manfred Hugo Vock, Locust, both of N.J.

[73] Assignee: International Flavors & Fragrances Inc., New York, N.Y.

[22] Filed: Nov. 20, 1975

[21] Appl. No.: 633,800

Related U.S. Application Data

[63] Continuation-in-part of Ser. No. 485,554, July 3, 1974.

[52] U.S. Cl. .......................... 260/617 F; 131/17 R; 252/32; 252/132; 252/522; 260/617 R; 260/586 G; 426/650

[51] Int. Cl.$^2$ .......................... C07C 35/22

[58] Field of Search .......................... 260/617 F, 617 R

[56] References Cited

UNITED STATES PATENTS

| | | | |
|---|---|---|---|
| 3,879,466 | 4/1975 | Light | 260/617 F |
| 3,925,486 | 12/1975 | Greuter et al. | 260/617 F |

OTHER PUBLICATIONS

Murray et al, "Chem. Ab.", 79:146059d, (1973).
Schulte-Elte et al., "Chem. Ab.", 79:115743t, (1973).
Humgartner, et al., "Chem. Ab.", 77:61121b, (1972).
Ratcliff et al., "Chem. Ab.", 76:126155s, (1972).
Chow et al., "Chem. Ab.", 73:103784v, (1970).
Hansen et al., "Chem. Ab.", 69:26501p, (1968).

*Primary Examiner*—Norman Morgenstern
*Attorney, Agent, or Firm*—Arthur L. Liberman; Harold Haidt; Franklin D. Wolffe

[57] ABSTRACT

Processes and compositions for altering the flavor and/or aroma of consumable products including foods, tobacco and perfumes utilizing as the essential ingredient the novel organic tricyclic alcohol having the formula:

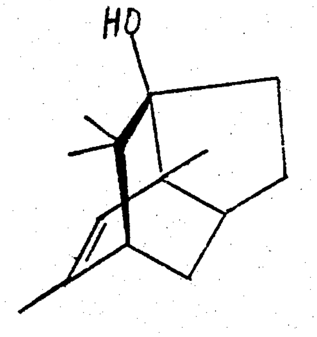

and a process for preparing the above-mentioned compounds involving first intimately admixing a tetramethyl cyclohexadienone having the structure:

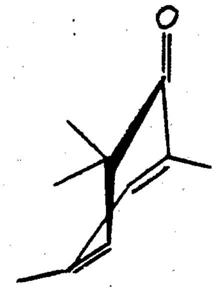

with 3-butenyl lithium having the structure:

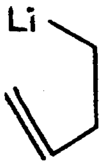

thereby forming a triene compound having the structure:

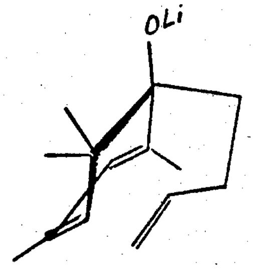

and then heating the triene compound at an elevated temperature and pressure thereby producing a metallo tricyclic compound having the structure:

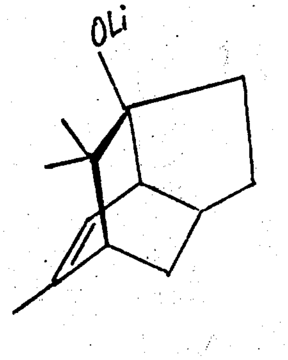

which is then hydrolyzed to form the tricyclic alcohol of this invention having the structure:

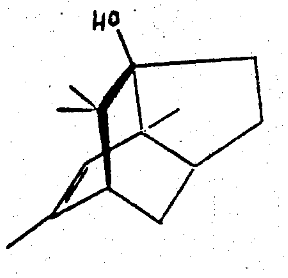

3 Claims, 2 Drawing Figures

FRACTION 3 Trap FROM EXAMPLE I

FRACTION 3 Trap FROM EXAMPLE I

TRICYCLIC ALCOHOLS AND LITHIUM SALTS THEREOF

Figure 1:
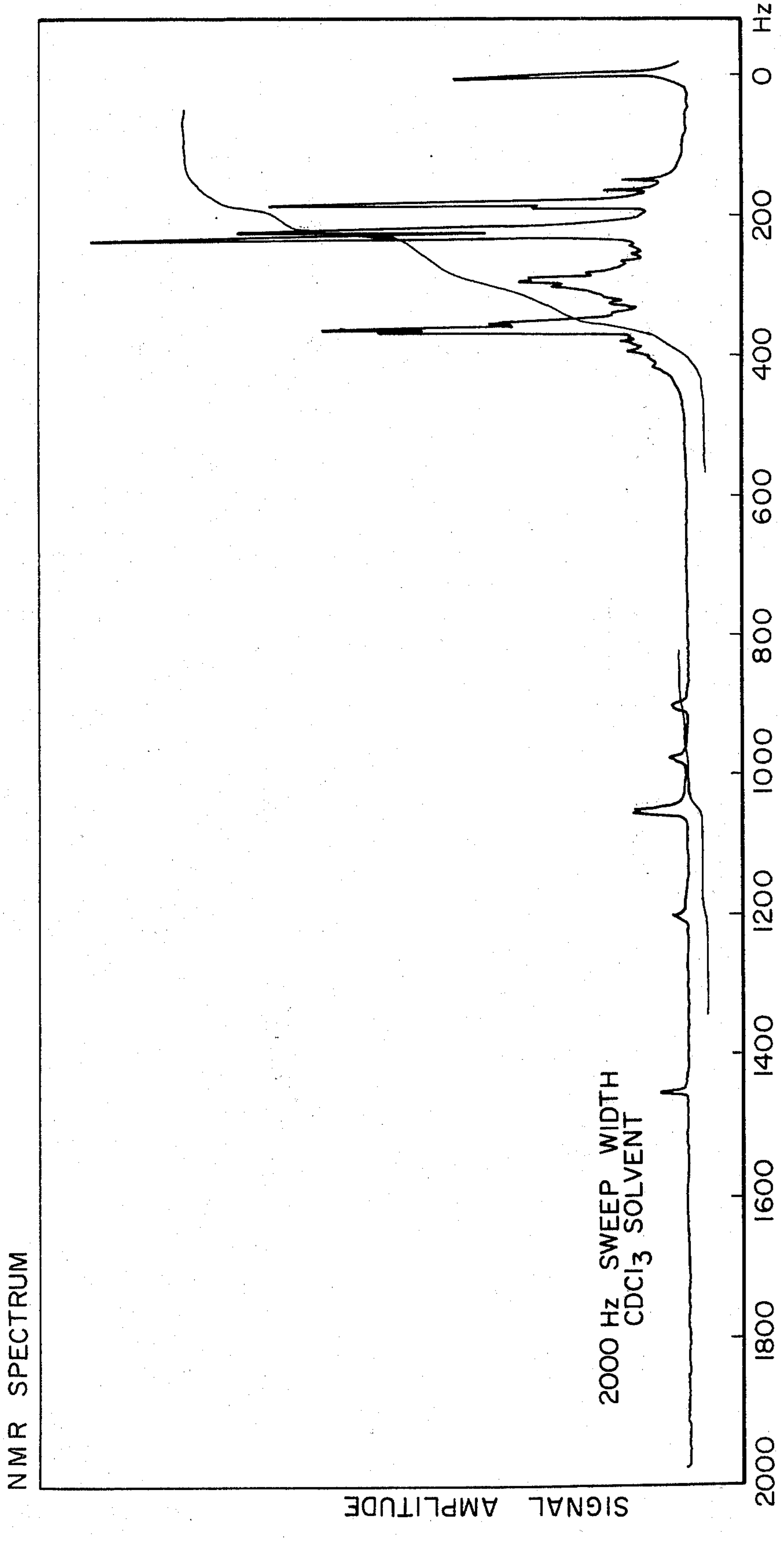

This application is a continuation-in-part of U.S. application for Letters Patent Ser. No. 485,554 filed on July 3, 1974.

BACKGROUND OF THE INVENTION

Materials including mixtures of natural products which can provide patchouli-like, earthy, woody, peppery and camphoraceous fragrance notes are known in the art of perfumery. Many of the natural materials which provide such fragrances and contribute desired nuances to perfumery compositions are high in cost, vary in quality from one batch to another and/or are generally subject to the usual variations of natural products.

There is accordingly a continuing effort to find synthetic materials which will replace the essential fragrance notes provided by natural essential oils or compositions thereof. Unfortunately, many of these synthetic materials either have the desired nuances only to a relatively small degree or else contribute undesirable or unwanted odor to the compositions. The search for materials which can provide a more refined patchouli-like fragrance has been difficult and relatively costly in the areas of both natural products and synthetic products.

Buchi et al., 83 J. Am. Chem. Soc. 927 (1961), shows the production of a material called "patchoulione" which is stated to be octahydro-1,4,9,9-tetramethyl-3a,7-methanoazulen-5-(4H)-one having the structure:

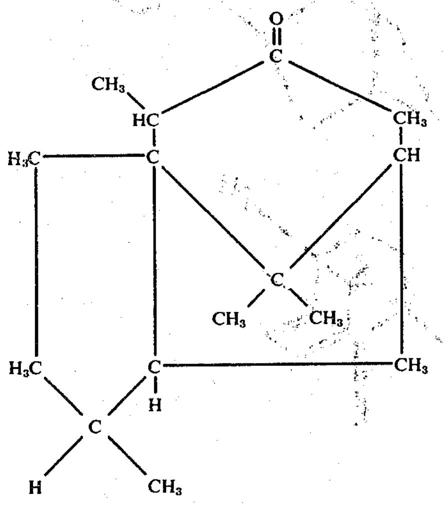

U.S. Pat. No. 3,748,284 issued on July 24, 1973 discloses perhydro derivatives of methanoazulen as having camphoraceous woody fragrances and having the ability to impart this fragrance to perfumed compositions and perfumed articles. The compounds disclosed are:

a. Octahydro-1,4,9,9-tetramethyl-4,7-methanoazulen-3(2H)-one having the structure:

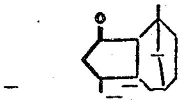

b. Octahydro-1,4,9,9-tetramethyl-- -methanoazulen-2(3H)-one having the structure:

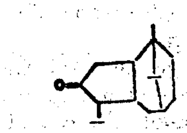

; and c. Octahydro-1,4,9,9-tetramethyl-4,7-methanoazulen-8(7H)-one having the structure:

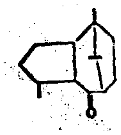

Umarani et al., Sept./Oct. 1969, P. & E.O.R., 307 discloses two compounds relevant to the instant case: "isopatchoulinol" having the structure:

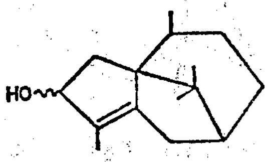

and "patchouli alcohol" having the structure:

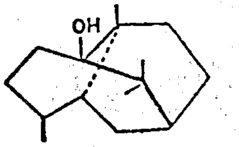

In addition, artificial flavoring agents for foodstuffs have received increasing attention in recent years. In many years, such food flavoring agents have been preferred over natural flavoring agents at least in part due to their diminished cost and their reproducible flavor qualities. For example, natural food flavoring agents such as extracts, concentrates and the like are often subject to wide variations due to changes in the quality, type and treatment of the raw materials. Such variations can be reflected in the end product and result in unfavorable flavor characteristics in said end product. Additionally, the presence of the natural product in the ultimate food may be undesirable because of increase tendency to spoil. This is particularly troublesome in food and food uses where such products as dips, soups, chips, sausages, gravies and the like are apt to be stored prior to use.

The fundamental problem in creating artificial flavor agents is that the artificial flavor to be achieved be as natural as possible. This generally proves to be a difficult task since the mechanism for flavor development in many foods is not completely known. This is noticeable in products having nutty, earthy, woody-balsamic, fresh walnut-kernel, patchouli, eucalyptus, incense-like, walnut-skin flavor and cooling characteristics.

Reproduction of nutty, earthy, woody-balsamic, fresh walnut-kernel and walnut-skin flavor and aroma has been the subject of long and continuing searches by those engaged in a production of foodstuffs and beverages. The severe shortage of food in many parts of the world has given rise to the development of previously unused sources of protein which are unpalatable. Accordingly, the need has arisen for the use of flavoring materials which will make such sources of protein palatable to human sensory organs.

Even more desirable is a product that can serve to substitute for difficult-to-obtain natural perfumery oils and at the same time substitute for natural flavoring ingredients in both foodstuffs as well as in tobacco.

Mirrington and Schmalzl 37 *J. Org. Chem.* No. 18, 1972, pages 2871–2877 discloses the isolation of (−) patchouli alcohol having the structure:

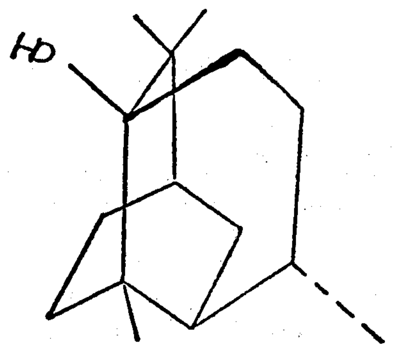

An article by Corey and Wipke entitled "Computer-Assisted Design of Complex Organic Syntheses" appearing in 166 Science 178 (1969) sets forth, interalia, the sequence of reactions leading to compounds having the structures:

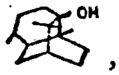 , 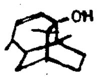 , 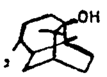 and 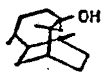

One of these reaction sequences involves performing the reactions:

(A)

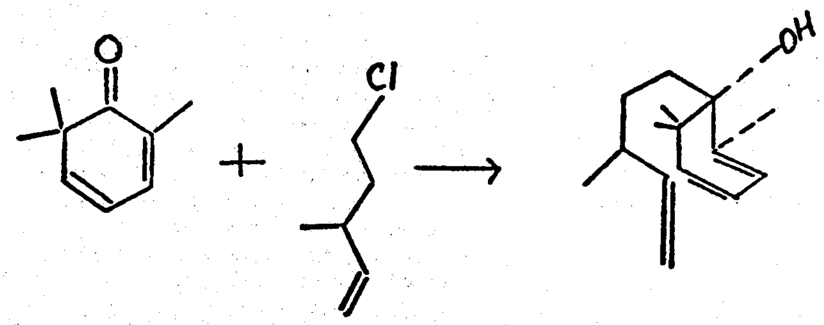

(B)

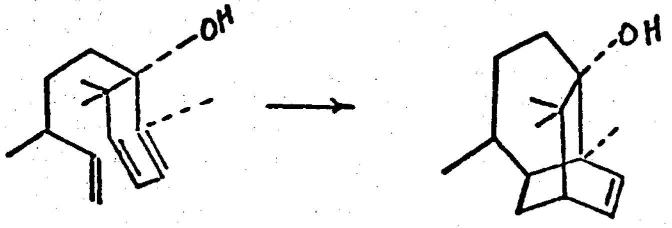

(C)

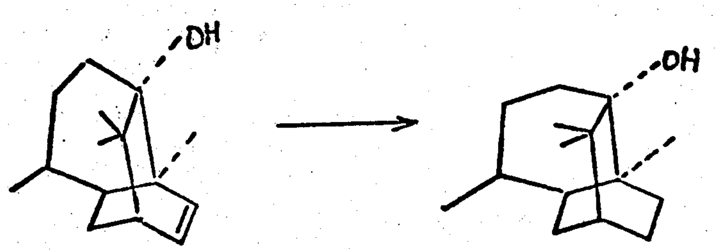

However, syntheses of lower methylene homologues of such compounds have not been disclosed in the prior art.

Danishevsky and Dumans 1968 Chemical Communication, Pages 1287–1288 discloses the synthesis of racemic patchouli alcohol and epi patchouli alcohol having the structure:

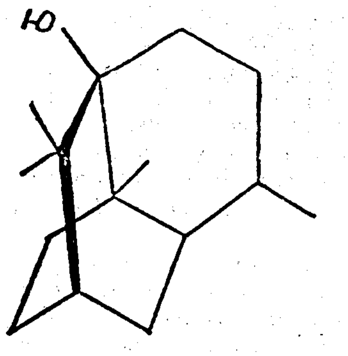

by means of cyclization of a compound having the structure:

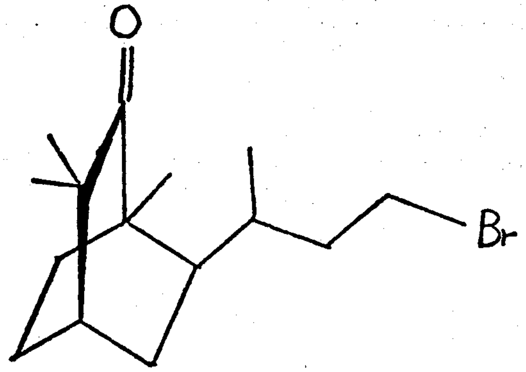

The use in perfumery of the compound having the structure:

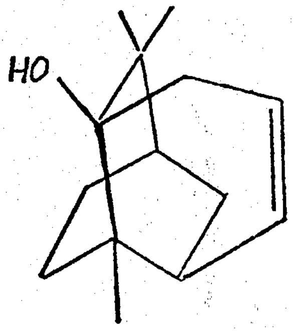

("norpatchoulinol") is disclosed in the following patents:

1. Belgium Pat. No. 788,301 issued Mar. 1, 1973
2. German Offenlegungschrift No. 2,242,913 published Mar. 8, 1973
3. Dutch published Application No. 72/11760 published Mar. 5, 1973

A product of the reduction of this compound is also disclosed ("dihydro-norpatchoulinol"). This product has the structure:

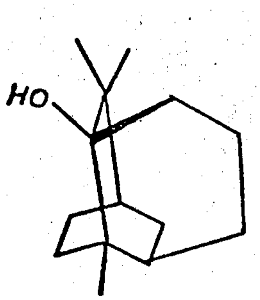

The compounds of our invention have properties considered to be unobvious, unexpected and advantageous with respect to the properties of the above-mentioned prior art compounds.

In addition, application for U.S. Letters Patent Ser. No. 436,848 filed on Jan. 28, 1974 now U.S. Pat. No. 3,907,908, claims processes and compositions for altering the flavor and/or aroma of consumable products including foods, tobacco and perfumes utilizing as the essential ingredient at least one organic tricyclic alcohol having the formula:

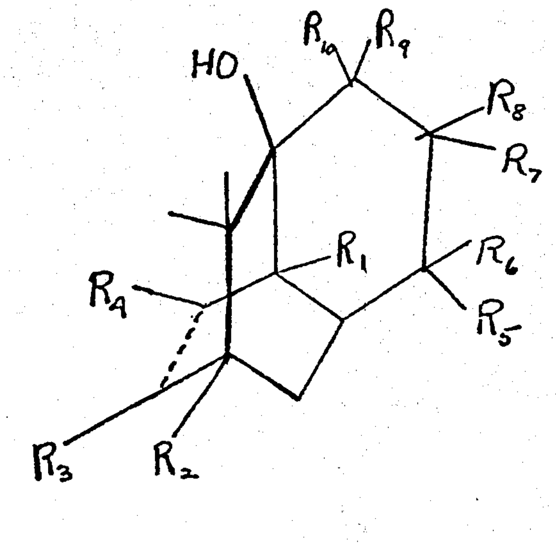

wherein each of $R_1$, $R_2$, $R_3$, $R_4$, $R_5$, $R_6$, $R_7$, $R_8$, $R_9$ and $R_{10}$ is selected from the group consisting of hydrogen and methyl; wherein the dashed line is a carbon-carbon single bond or a carbon-carbon double bond; wherein $R_1$ is limited to hydrogen when (i) the dashed line is a carbon-carbon single bond; (ii) $R_2$, $R_3$, $R_4$, $R_6$, $R_7$, $R_8$, $R_9$ and $R_{10}$ is hydrogen and (iii) $R_5$ is hydrogen or methyl and wherein when the dashed line is a carbon-carbon single bond, one of $R_3$ or $R_4$ is hydrogen; and processes for preparing the above-mentioned compounds and in addition compounds having similar structures, that is, when the dashed line is either a carbon-carbon single bond or a carbon-carbon double bond; $R_1$, $R_2$, $R_3$, $R_4$, $R_5$, $R_6$, $R_7$, $R_8$, $R_9$ and $R_{10}$ are each the same or different and each represents hydrogen and wherein when $R_3$ or $R_4$ is hydrogen the dashed line represents a carbon-carbon single bond and when $R_3$ and $R_4$ are both methyl, the dashed line represents a carbon-carbon double bond, involving first intimately admixing a methyl substituted cyclohexadienone having the structure:

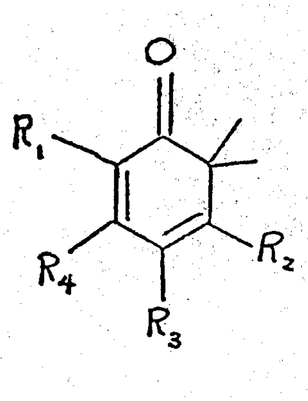

with an acetylenic compound having the structure:

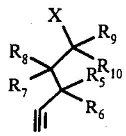

wherein X can be either hydroxyl, bromo or chloro thereby forming a diene compound having the structure:

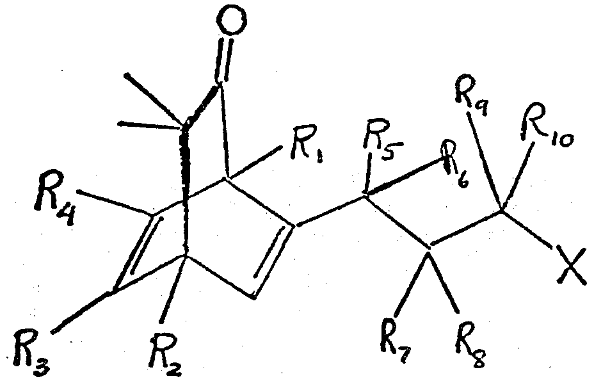

and then hydrogenating the diene compound with hydrogen in the presence of a hydrogenation catalyst thereby producing a ketone having the structure:

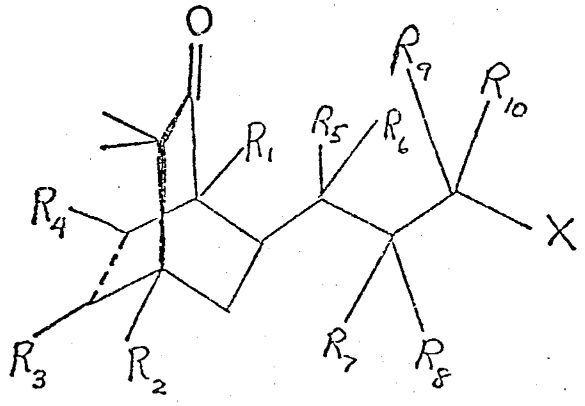

It is further disclosed that this ketone may either be immediately cyclized using an alkali metal such as sodium, potassium or lithium in the case of X being halogen, or when X is OH, the ketone is first halogenated with a halogenating agent to first form a compound having the structure:

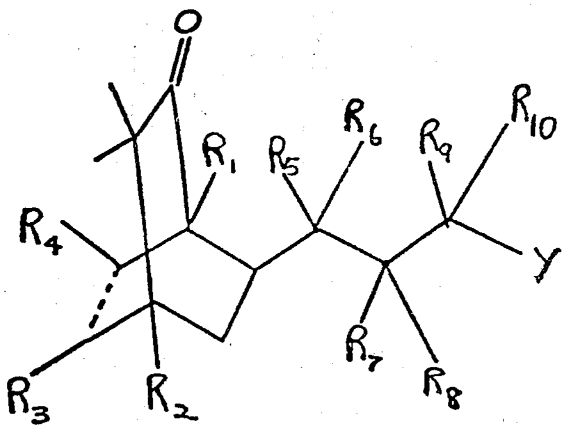

wherein Y is bromo or chloro and subsequently the halogenated compound may then be cyclized using a cyclizing agent.

The compounds, uses and processes claimed in Ser. No. 436,848 filed on Jan. 28, 1974, now U.S. Pat. No. 3,907,908, do not contemplate the lower methylene homologues thereof of the instant case.

Furthermore, application for U.S. Letters Patent Ser. No. 436,847 filed on Jan. 28, 1974 now U.S. Pat. No. 3,879,466, claims chemical compounds having the structure:

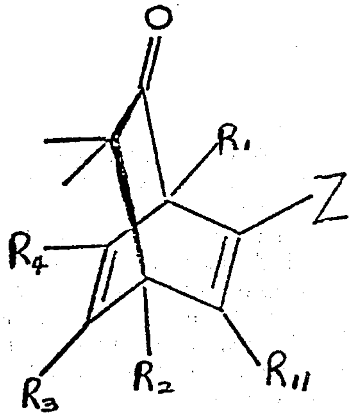

wherein Z is a moiety selected from the group consisting of:

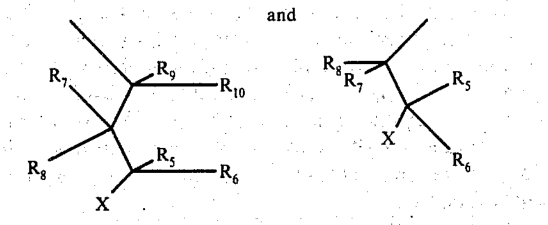

and wherein $R_1$, $R_2$, $R_3$, $R_4$, $R_5$, $R_6$, $R_7$, $R_8$, $R_9$ and $R_{10}$ are the same or different and each is selected from the group consisting of methyl and hydrogen and wherein $R_{11}$ is selected from the group consisting of metyl, ethyl and hydrogen; and wherein X is selected from the group consisting of bromo, chloro, hydroxyl, benzyloxyl and alkoxyl and a process for preparing such compounds involving intimately admixing a methyl substituted cyclohexadienone having the structure:

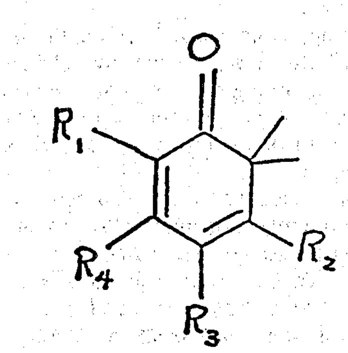

with one of the following acetylenic compounds having the structures:

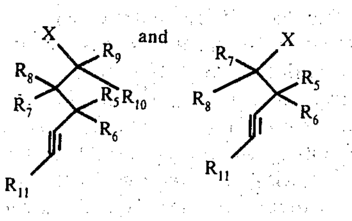

Neither the processes nor the compounds claimed in Ser. No. 436,847 filed on Jan. 28, 1974, now U.S. Pat. No. 3,879,466, are encompassed within the scope of the instant invention.

THE INVENTION

It has now been determined that a certain tricyclic alcohol is capable of imparting a variety of flavors and fragrances to various consumable materials. Briefly, our invention contemplates altering the flavors and/or fragrances of such consumable materials by adding thereto a small but effective amount of the one tricyclic alcohol having the structure:

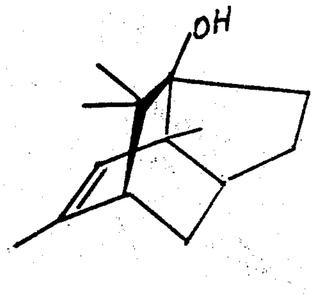

(having the name 2,3,3A,4,5,7A-hexahydro-6,7A,8,8-tetramethyl-1,5-methano-1H-inden-1-ol) and flavoring and fragrance compositions containing such tricyclic alcohol. The invention also contemplates a novel process for producing such compound.

The tricyclic alcohol produced according to the process of our invention, which is used in practicing the part of our invention concerning flavoring and fragrance compositions is actually a racemic mixture rather than an individual steroisomer, such as the case concerning isomers of patchouli alcohol which are so obtained from patchouli oil.

The compound of our invention has a strong patchoulilike, sweet, earthy, peppery, camphoraceous note and an earthy, patchouli, nutty, woody-like taste and aroma with incense-like, eucalyptus and cooling nuances in food flavors.

The tricyclic alcohol prepared according to the present invention can be obtained by means of a reaction sequence which comprises first intimately admixing a tetramethyl cyclohexadienone having the structure:

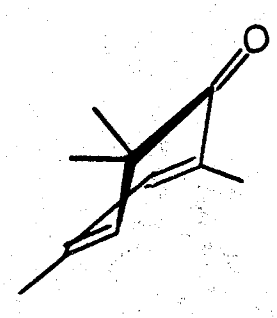

with 3-butenyl lithium having the structure:

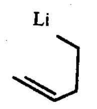

thereby forming a triene compound having the structure:

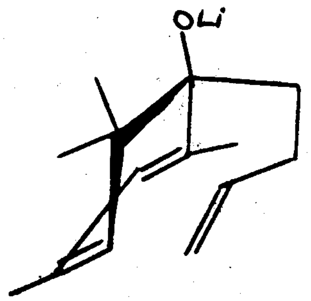

In this reaction, it is best to proceed at a reflux temperature in the range of 40°–90° C with the most preferred temperature range being 45° C, the refluxing temperature when using a diethyl ether reaction vehicle. The reaction is carried out in the presence of an inert solvent such as diethyl ether, benzene, hexane or cyclohexane (or any other inert solvent). Although, either the 3-butenyl lithium or the cyclohexadienone may be used in excess, it is preferred to use the 3-butenyl lithium in excess, the mole ratio of 3-butenyl lithium: cyclohexadienone preferred to be between 2:1 and 3:1.

The above-mentioned triene compound is then cyclized at a temperature of between 150° and 300° C and a pressure of from 250 up to about 500 psig using an inert solvent such as benzene, toluene or xylene.

The cyclization reaction gives rise to a metallo tricyclic compound having the structure:

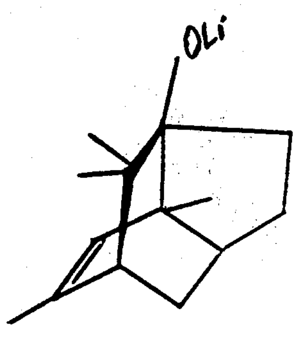

The metallo tricyclic compound is then hydrolyzed using water or, more preferably, dilute aqueous mineral acid for example dilute sulfuric acid.

When the final hydrolysis reaction is completed, the reaction mixture is "worked-up" using routine purification procedures including the unit operations of extraction, crystallization, drying and/or distillation.

The tricyclic compound of our invention can be obtained in purer form or in substantially pure form by conventional purification techniques. Thus, the product can be purified and/or isolated by distillation, extraction, crystallization, preparative chromatographic techniques, and the like. It has been found desirable to purify the tricyclic compound by fractional distillation by vacuum.

It will be appreciated from the present disclosure that the tricyclic compound according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting an existing flavor characteristic where the natural flavor is deficient in some regard or supplementing the existing flavor impression to modify the organoleptic character.

The term "enhance" is intended herein to mean the intensification (by use of the tricyclic alcohol of our invention) of a flavor or aroma note or nuance in a tobacco flavor or foodstuff or perfume composition or a perfumed article without changing the *quality* of said note or nuance.

A "flavoring composition" is taken to mean one which contributes a part of the overall flavor impression by supplementing or fortifying a natural or artificial flavor in a material or one which supplies substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt, alcoholic, and other beverages, milk and dairy products, seafoods including fish, crustaceans, mollusks, and the like, candies, vegetables, cereals, soft drinks, snacks, dog and cat food, other veterinary products, and the like.

The tricyclic compound of our invention is also a useful tobacco flavorant and flavor enhancer.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products in which the tricyclic compounds of our invention are useful include those designed or used for smoking such as in cigarette, cigar and pipe tobacco, as well as products such as snuff, chewing tobacco, and the like.

When the tricyclic compound of this invention is used in a flavoring composition, it can be combined with conventional flavoring materials or adjuvants. Such co-ingredients or flavoring adjuvants are well known in the art for such use and have been extensively described in the literature. Requirements of such adjuvant materials are: (1) that they be non-reactive with the tricyclic compound of our inventions; (2) that they be organoleptically compatible with the tricyclic compound of our invention whereby the flavor of the ultimate consumable material to which the tricyclic compound is added is not detrimentally affected by the use of the adjuvant and (3) that they be ingestibly acceptable, and thus non-toxic or not otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids; alcohols, including primary and secondary alcohols; esters; carbonyl compounds including ketones and aldehydes; lactones; other cyclic organic materials including benzene derivatives, alicyclic compounds, heterocyclics such as furans, pyridines, pyrazines and the like; sulfur-containing materials including thiols, sulfides, disulfides and the like; proteins; lipids, carbohydrates; so-called flavor potentiators such as monosodium glutamate, guanylates, and inosinates; natural flavoring materials such as cocoa, vanilla and caramel; essential oils and extracts such as anise oil; clove oil; and the like; and artificial flavoring materials such as vanillin; and the like.

Specific preferred flavor adjuvants are as follows:
Ethyl-2-methyl butyrate;
Vanillin;
Butyl valerate;
2,3-Diethyl pyrazine;
Methyl cyclopentenolone;
Benzaldehyde;
Valerian Oil Indian; and
Propylene glycol When used in perfumery, in order to alter, modify or enhance the aroma of perfume compositions, or perfumed articles the tricyclic alcohol of our invention can be used to contribute patchouli-like, earthy, peppery, woody and camphoraceous aromas. As an olfactory agent the tricyclic compound of this invention can be formulated into or used as a component of a "perfume composition".

The term perfume composition is used herein to mean a mixture of organic compounds, including, for example, alcohols, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh smelling materials.

In perfume compositions, the individual component will contribute its particular olfactory characteristics but the overall effect of the perfume composition will be the sum of the effect of each ingredient. Thus, the tricyclic alcohol of this invention can be used to alter, modify or enhance the aroma characteristics of a perfume composition, for example, by highlighting or moderating the olfactory reaction contributed by another ingredient in the composition.

The amount of the tricyclic alcohol of this invention which will be effective in perfume compositions depends on many factors, including the other ingredients, their amounts and the effects which are desired. It has been found that perfume compositions containing as little as 1 percent of the tricyclic alcohol of this invention, or even less, can be used to impart a patchouli scent with earthy, woody, peppery and camphoraceous notes to soaps, cosmetics, and the other products. The amount employed can range up to 50% or higher and will depend on considerations of cost, nature of the end product, the effect desired on the finished product and particular fragrance sought.

The tricyclic alcohol of this invention can be used alone or in a perfume composition as an olfactory component in detergents, and soaps, space odorants and deodorants; perfumes; colognes; toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like. When used as an olfactory component of a perfumed article, as little as 0.01 percent of one or more of the tricyclic alcohol will suffice to impart a patchouli aroma with earthy, woody, peppery and camphoraceous notes. Generally, no more than 0.5 percent is required.

In addition, the perfume composition can contain a vehicle or carrier for the tricyclic alcohol alone or with other ingredients. The vehicle can be a liquid such as an alcohol such as ethanol, a glycol such as propylene glycol, or the like. The carrier can be an absorbent solid such as a gum or components for encapsulating the composition.

The following examples are given to illustrate embodiments of the invention as it is presently preferred to practice it. It will be understood that these examples are illustrative, and the invention is not to be considered as restricted thereto except as indicated in the appended claims.

EXAMPLE I

Reaction Sequence:

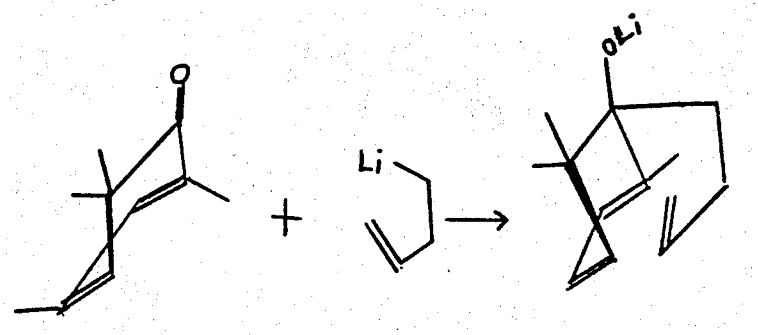

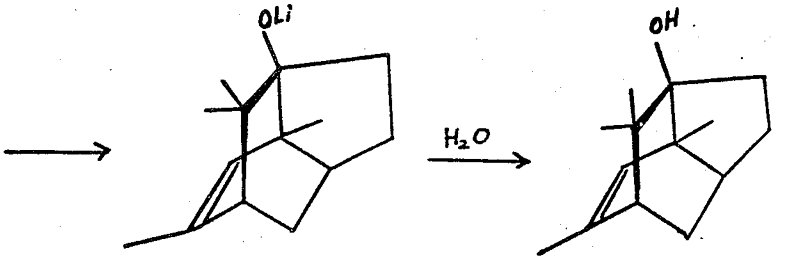

Procedure

Part A: Production of 3-butenyl lithium

A 100 ml microflask fitted with a thermometer, a reflux condenser, a nitrogen inlet and a magnetic stirrer is charged with 2.3 gm of Li shot and 50 ml of anhydrous diethyl ether. The contents of the microflask is heated to reflux and maintained at reflux for a period of 2 hours. 4-Bromo-1-butene is then added dropwise over a 45 minute period during refluxing of the reaction mass at a temperature of 45° C.

Part B: Production of triene compound

To the diethyl ether/3-butenyl lithium reaction mixture produced according to the procedure of part A, 2,2,4,6-tetramethyl-3,5-cyclohexadien-1-one is added with maintaining the reaction mass at reflux. The refluxing is then continued for a period of 7 hours. The reaction mass is then filtered in order to remove unreacted lithium.

Part C: Cyclization of triene compound to produce metallo tricyclic compound

The filtered reaction mass produced according to the procedure of part B is admixed with 300 ml benzene and the resulting mixture is charged to an autoclave. The autoclave is then sealed and the contents are heated to 200° C and maintained at 200° C and 280 psig pressure for a period of 6 hours. At the end of the six hour period, the autoclave is opened and the contents are removed.

Part D: Hydrolysis of the metallo tricyclic compound

The reaction mass produced in part C is admixed with an equal volume of water thereby forming two phases: (1) an organic phase and (2) an aqueous phase. The phases are separated. The aqueous phase is then extracted with three 25 ml portions of diethyl ether and the resulting ether extracts are then combined with the organic phase. The bulked organic phase is then washed with two 50 ml portions of water and is dried over anhydrous $MgSO_4$. The diethyl ether is then stripped off and the resulting concentrate is vacuum distilled on a 6 inch microvigreux column after adding to the concentrate 5.3g of a 50:50 mixture of Primol and Ionox.

The fractional distillation data is as follows:

| Fraction No. | Vapor Temperature | Liquid Temperature | Pressure (mm. Hg) | Weight of Fraction |
|---|---|---|---|---|
| 1 | 35–83° C | 95–120° C | 0.35 | 2.2 g |
| 2 | 87° C | 150° C | 0.35 | 3.2 |
| 3 | 100–145° C | 150–210° C | 0.30 | 1.7 |

Fraction 3 is analyzed using preparative GLC followed by NMR, IR and mass spectral analyses of the traps.

The major GLC peak of Fraction 3 is confirmed by IR, NMR and mass spectral analyses to have the structure:

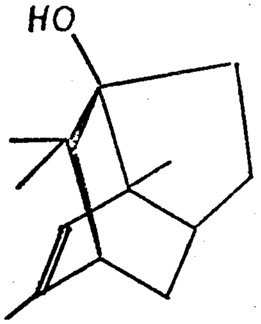

(2,3,3A,4,5,7A-hexahydro-6,7A,8,8-tetramethyl-1,5-methano-1H-inden-1-ol)

This material has a sweet, earthy, woody fragrance with a fine patchouli note and peppery and camphoraceous nuances with respect to its use in perfume compositions and perfumed articles; and a patchouli-like, fresh walnut kernel-like and incense-like camphoraceous aroma with patchouli-like, camphoraceous, eucalyptus, fresh walnut kernel, walnut skin, woody balsamic and cooling flavor characteristics with respect to its use in foodstuff flavors.

The NMR analysis is as follows:

| Peak | Interpretation | |
|---|---|---|
| 5.24 ppm (broad) | olefinic proton | 1H |
| 2.20 – 1.22 (m) | $-CH_2-$, $Hc-$ | |
| 1.80 (d, j is approximately 2Hz) | $=C-CH_3$ | 3H |
| 1.13 (s) | quaternary methyl protons | 9H |
| 1.08 (s) | quaternary methyl protons | |
| 0.90 (s) | quaternary methyl protons | |

Th nuclear magnetic resonance (NMR) spectrum for the Fraction No. 3 Trap is set forth in FIG. 1.

The IR analysis is as follows:

1065 $cm^{-1}$
1085
1355
1360
1380
1445
2860
2920
3460

Figure 2:
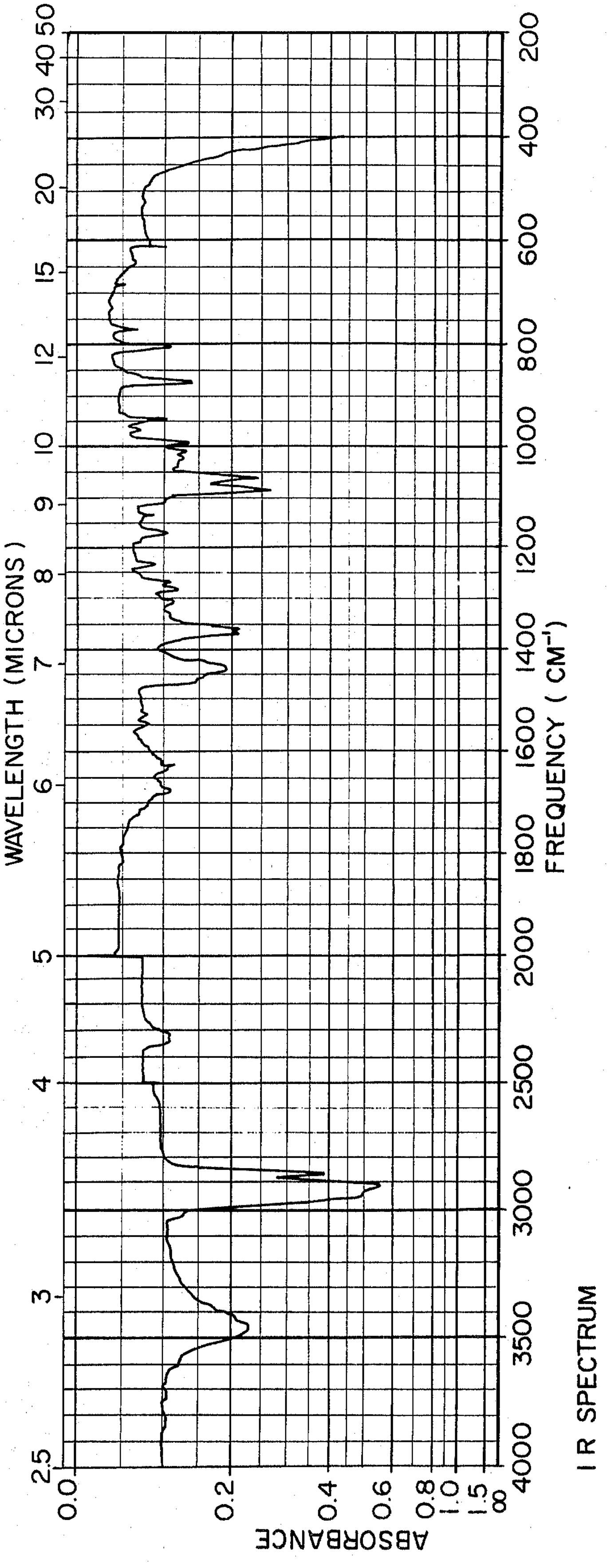

The infra red spectrum for the Fraction No. 3 Trap is set forth in FIG. 2.

EXAMPLE II

Patchouli Perfume Formulation

The following mixture is prepared:

| Ingredient | Parts by Weight |
|---|---|
| Orange Oil | 50 |
| Bergamot Oil | 20 |
| Lime Oil | 100 |
| Neroli Oil | 5 |
| 4-(4-Methyl-4-hydroxyamyl) $\Delta^3$-cyclohexene carboxaldehyde | 5 |
| 2,3,3A,4,5,7A-hexahydro-6,7A,8,8-tetramethyl-1,5-methano-1H-inden-1-ol (prepared according to the process of Example I, supra) | 200 |
| 1′,2′,3′,4′,5′,6′,7′,8′-octahydro 2′,3′,8′,8′-tetramethyl-2′-aceto-naphthone isomer mixture produced according to the process of Example VII of Application for U.S. Letters Pat. No. 434,948 filed on January 21, 1974, now U.S. Pat. No. 3,911,018 issued on October 7, 1975 | 50 |
| Gamma Methyl Ionone | 20 |
| 1-acetyl-2,5,5-trimethylcycloheptane produced according to U.S. Pat. No. 3,869,411 issued on March 4, 1975 | 50 |

The 2,3,3A,4,5,7A-hexahydro-6,7A,8,8-tetramethyl-1,5-methano-1H-inden-1-ol produced according to the process of Example I, when added to this formulation in the amount indicated; and also in amounts up to 30% by weight of the total mixture; or in amounts as little as 1.0% by weight of this mixture, imparts a dominating, warm, earthy, peppery, camphoraceous character akin to patchouli to this patchouli perfume composition.

EXAMPLE III

Preparation of Soap Compositions

Part A

A total of 100 g of soap chips produced from unperfumed sodium base toilet soap made from tallow and coconut oil is mixed with 1 g of 2,3,3A,4,5,7A-hexahydro-6,7A,8,8-tetramethyl-1,5-methano-1H-inden-1-ol (produced according to Example I) until a substantially homogeneous composition is obtained. The soap composition manifests a patchouli-like character having peppery, earthy, woody and camphoraceous notes.

Part B

A total of 100 g of soap chips produced from unperfumed sodium base toilet soap made from tallow and coconut oil is mixed with 1 g of the perfume composition set forth in Example II until a substantially homogeneous composition is obtained. The soap composition manifests a characteristic patchouli aroma having a dominating, warm, earthy, peppery, camphoraceous character.

EXAMPLE IV

Preparation of a Detergent Composition

A total of 100 g of a detergent powder sold under trademark "RINSO" are mixed with 0.15 g of a perfume composition containing the mixture prepared according to Example II until a substantially homogeneous composition having a patchouli fragrance with a dominating, warm, earthy, peppery, camphoraceous character is obtained.

EXAMPLE V

Preparation of a Cosmetic Base

A cosmetic powder is prepared by mixing 100 g of talcum powder with 0.25 g of the perfume composition of Example II in a ball mill. A second cosmetic powder is similarly prepared except that the mixture produced in Example II is replaced with the product produced in Example I, 2,3,3A,4,5,7A-hexahydro-6,7A,8,8-tetramethyl-1,5-methano-1H-inden-1-ol. The cosmetic powder containing the material of Example II has a patchouli fragrance with a dominating, warm, earthy, peppery and camphoraceous character. The cosmetic powder produced using the material of Example I has a warm natural patchouli-like character with earthy, woody, peppery and camphoraceous notes.

EXAMPLE VI

Liquid Detergent Containing Octahydro-7A,8,8-Trimethyl-1,5-Methano-1H-Inden-1-Ol Concentrated liquid detergents with a warm patchouli-like odor having earthy, woody and camphoraceous notes containing 0.2%, 0.5% and 1.2% of the product produced in accordance with the process of Example I, 2,3,3A,4,5,7A-hexahydro-6,7A,8,8-tetramethyl-1,5-methano-1H-inden-1-ol, are prepared by adding appropriate quantities of 2,3,3A,4,5,7A-hexahydro-6,7A,8,8-tetramethyl-1,5-methano-1H-inden-1-ol to the liquid detergent known as P-87. The warm patchouli aroma of the liquid detergent increases with increasing concentration of the 2,3,3A,4,5,7A-hexahydro-6,7A,8,8-tetramethyl-1,5-methano-1H-inden-1-ol of this invention.

EXAMPLE VII

Preparation of Cologne and Handkerchief Perfume

The composition of Example II is incorporated in a cologne having a concentration of 2.5% in 85% aqueous ethanol; and into a handkerchief perfume in a concentration of 20% (in 95% aqueous ethanol). The use of the composition of Example II affords a distinct and definite patchouli aroma having a warm, earthy, peppery and camphoraceous character to the handkerchief perfume and to the cologne.

EXAMPLE VIII

Cologne and Handkerchief Perfume

The 2,3,3A,4,5,7A-hexahydro-6,7A,8,8-tetramethyl-1,5-methano-1H-inden-1-ol produced by the process of Example I is incorporated into a perfume having a concentration of 2.5% in 85% ethanol; and into a handkerchief perfume in a concentration of 10% (in 95% aqueous ethanol). The 2,3,3A,4,5,7A-hexahydro-6,7A,8,8-tetramethyl-1,5-methano-1H-inden-1-ol produced in Example I affords a distinct and definite warm patchouli-like aroma (with earthy, peppery, woody and camphoraceous notes) to the handkerchief perfume and to the cologne.

EXAMPLE IX

Flavor Composition

The following basic walnut flavor formulation is prepared:

| Ingredients | Parts by Weight |
|---|---|
| Ethyl-2-methyl butyrate | 10 |
| Vanillin | 40 |
| Butyl valerate | 40 |
| 2,3-Diethyl pyrazine | 5 |
| Methyl Cyclopentenolone | 80 |
| Benzaldehyde | 60 |
| Valerian Oil Indian (1% in 95% aqueous ethanol alcohol) | 0.5 |
| Propylene Glycol | 764.5 |

2,3,3A,4,5,7A-hexahydro-6,7A,8,8-tetramethyl-1,5-methano-1H-inden-1-ol produced by the process of Example I is added to the above formulation at the rate of 1.5%. This formulation is compared to a formulation which does not have 2,3,3A,4,5,7A-hexahydro-6,7A,8,8-tetramethyl-1,5-methano-1H-inden-1-ol added to it, at the rate of 20 ppm in water. The formulation containing 2,3,3A,4,5,7A-hexahydro-6,7A,8,8-tetramethyl-1,5-methano-1H-1-ol has a "woody-balsamic", fresh walnut kernel, walnut skin-like, eucalyptus and cooling taste, and in addition, has a fuller mouthfeel and longer lasting taste. The flavor that has added to it 2,3,3A,4,5,7A-hexahydro-6,7A,8,8-tetramethyl-1,5-methano-1H-inden-1-ol is preferred by a group of flavor panelists, and they consider it to be a substantially improved walnut flavor.

EXAMPLE X

Beverage

The addition of 2,3,3A,4,5,7A-hexahydro-6,7A,8,8-tetramethyl-1,5-methano-1H-inden-1-ol prepared by the process of Example I at the rate of 0.3 ppm to a commercial Cola beverage gives the beverage a fuller woody-balsamic long lasting taste and adds to the pleasant top notes of the beverage. When comparing the Cola beverage containing 2,3,3A,4,5,7A-hexahydro-6,7A,8,8-tetramethyl-1,5-methano-1H-inden-1-ol to one having the same formula but not containing 2,3,3A,4,5,7A-hexahydro-6,7A,8,8-tetramethyl-1,5-methano-1H-inden-1-ol, a five member bench panel prefers the beverage containing the 2,3,3A,4,5,7A-hexahydro-6,7A,8,8-tetramethyl-1,5-methano-1H-inden-1-ol.

EXAMPLE XI

Tobacco Flavor Formulation

Cigarettes are produced using the following tobacco formulation:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| $H_2O$ | 5.3 |

At the rate of 0.2%, the following tobacco flavor formulation is applied to all of the cigarettes produced with the above tobacco formulation.

| Ingredients | Parts by Weight |
|---|---|
| Ethyl butyrate | .05 |
| Ethyl valerate | .05 |
| Maltol | 2.00 |
| Cocoa Extract | 26.00 |
| Coffee Extract | 10.00 |
| Ethyl Alcohol (95%) | 20.00 |
| $H_2O$ | 41.90 |

To 50% of the cigarettes, 10 and 20 ppm of 2,3,3A,4,5,7A-hexahydro-6,7A,8,8-tetramethyl-1,5-methano-1H-inden-1-ol are added. These cigarettes are hereinafter called "experimental" cigarettes and the cigarettes without the 2,3,3A,4,5,7A-hexahydro-6,7A,8,8-tetramethyl-1,5-methano-1H-inden-1-ol are hereinafter called "control" cigarettes. The control and experimental cigarettes are then evaluated by paired comparison and the results are as follows:

a. In aroma, the experimental cigarettes are found to be more aromatic.
b. In smoke flavor, the experimental cigarettes are found to be more aromatic, more sweet, more bitter, more green, richer and slightly less harsh in the mouth and more cigarette tobacco-like than the control cigarettes.

The experimental cigarettes containing 20 ppm of 2,3,3A,4,5,7A-hexahydro-6,7A,8,8-tetramethyl-1,5-methano-1H-inden-1-ol are found to be woody, slightly chemical and mouth-coating in the smoke flavor.

All cigarettes both control and experimental, are evaluated for a smoke flavor with 20 mm cellulose acetate filter. 2,3,3A,4,5,7A-hexahydro-6,7A,8,8-tetramethyl-1,5-methano-1H-inden-1-ol enhances the tobacco-like taste of the blended cigarette.

What is claimed is:

1. An organic tricyclic alcohol having the formula:

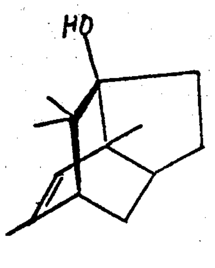

2. A metallo tricyclic compound having the formula:
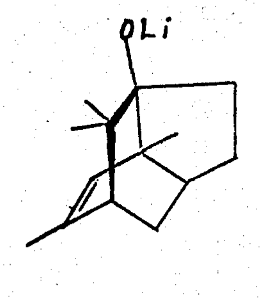
3. A triene compound having the structure:
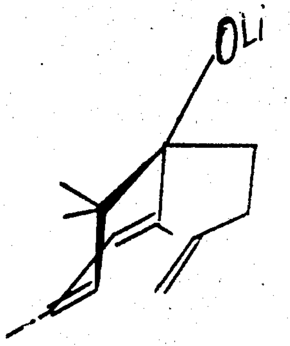
* * * * *